(12) United States Patent
Houghton et al.

(10) Patent No.: US 7,879,868 B2
(45) Date of Patent: Feb. 1, 2011

(54) USE OF IMATINIB (GLIVEC, STI-571) TO INHIBIT BREAST CANCER RESISTANCE PROTEIN (BCRP)-MEDIATED RESISTANCE TO THERAPEUTIC AGENTS

(75) Inventors: Peter J. Houghton, Memphis, TN (US); Peter Traxler, Schönenbuch (CH)

(73) Assignee: Novartis AG, Basel (CH)

( * ) Notice: Subject to any disclaimer, the term of this patent is extended or adjusted under 35 U.S.C. 154(b) by 197 days.

(21) Appl. No.: 10/530,618

(22) PCT Filed: Oct. 10, 2003

(86) PCT No.: PCT/EP03/11271

§ 371 (c)(1),
(2), (4) Date: Feb. 23, 2006

(87) PCT Pub. No.: WO2004/032925

PCT Pub. Date: Apr. 22, 2004

(65) Prior Publication Data

US 2006/0135527 A1 Jun. 22, 2006

Related U.S. Application Data

(60) Provisional application No. 60/417,915, filed on Oct. 11, 2002.

(51) Int. Cl.
*A01N 43/54* (2006.01)
*A01N 43/42* (2006.01)
*A61K 31/505* (2006.01)
*A61K 31/44* (2006.01)

(52) U.S. Cl. .................... 514/275; 514/283
(58) Field of Classification Search ............ 514/275, 514/283
See application file for complete search history.

(56) References Cited

U.S. PATENT DOCUMENTS 5,521,184 A * 5/1996 Zimmermann ......... 514/252.11
6,245,759 B1 * 6/2001 Bilodeau et al. ......... 514/233.2

OTHER PUBLICATIONS

Suggitt and Bibby, Clinical Cancer Research, 2005, vol. 11, 971-981.*
Houghton et al., "Imatinib mesylate (STI571, Gleevec) is a potent inhibitor of BCRP (ABCG2) and reverses topotecan resistance in vitro," Abstract No. 1959, Proceedings of the American Association for Cancer Research, vol. 44, Mar. 2003 Abstract.
Litman et al., "From MDR to MXR: new understanding of multidrug resistance systems, their properties and clinical significance," Cellular and Molecular Life Sciences, vol. 58, pp. 931-959 (2001).
Lage et al., "Effect of the breast-cancer resistance protein on atypical multidrug resistance," The Lancet Oncology, vol. 1, pp. 169-175 (2000).
Ross D.D., "Novel mechanisms of drug resistance in leukemia," Leukemia, vol. 14, pp. 467-473 (2000).
Wu et al., "Drug-resistant proteins in breast cancer: recent progress in multidrug resistance," Ai Zheng, vol. 22(4), pp. 441-444 (2003) Abstract.
Tan et al., "Multidrug resistance transporters and modulation," Current Opinion in Oncology 2000, vol. 12, pp. 450-458 (2000).
Kawabata et al., "Breast Cancer Resistance Protein Directly Confers SN-38 Resistance of Lung Cancer Cells," Biochemical and Biophysical Resarch Communications, vol. 280, pp. 1216-1223 (2001).
Erlichman et al., "The HER Tyrosine Kinase Inhibitor CI1033 Enhances Cytotoxicity of 7-Ethyl-10-hydroxycamptothecin and Topotecan by Inhibiting Breast Cancer Resistance Protein-mediated Drug Efflux," Cancer Research, vol. 61, pp. 739-748 (2001).
Sparreboom et al., "Pharmacogenomicas of ABC transporters and its role in cancer chemotherapy," Drug Resistance Updates 6, pp. 71-84 (2003).
J. A. Fagin, "Perspective: Lessons learned from olecular genetic studies of thyroid cancer: Insights into pathogenesis and tumor-specific therapeutic targets," Endocrinology, vol. 143(6), pp. 2025-2028 (2002).
Levitzki, "Tyrosine kinases as targets for cancer therapy," European Journal of Cancer, vol. 38, pp. S11-S18 (2002).
B. Selle et al., "ABL-specific tyrosine kinase inhibitor imatinib as salvage therapy in a child with Philadelphia chromosome-positive acute mixed lineage leukemia (AMLL)," Leukemia, vol. 16(7), pp. 1393-1395 (2002).
R. Capdeville et al., "Imatinib: the first 3 years," European Journal of Cancer, vol. 38, pp. S77-S82 (2002).
Y. Kano et al., "In vitro cytotoxic effects of a tyrosine kinase inhibitor STI571 in combination with commonly used antileukemic agents," Blood vol. 97(7), pp. 1999-2007 (2001).
J. Topaly et al., "Synergistic activity of STI571 with chemotherapeutic drugs and irradiation," Blood, vol. 96(11), p. 736A (2000).

* cited by examiner

*Primary Examiner*—Frederick Krass
*Assistant Examiner*—Benjamin Packard
(74) *Attorney, Agent, or Firm*—Ann R. Pokalsky, Esq.; Dilworth & Barrese, LLP

(57) ABSTRACT

The present invention relates to the use of imatinib of the following formula

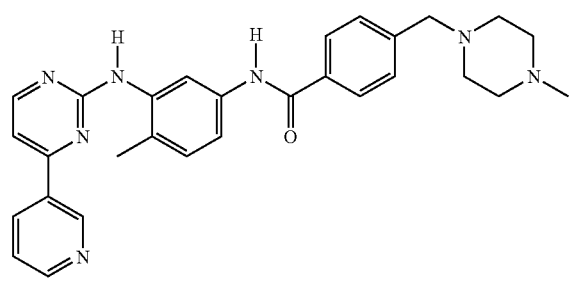

or a pharmaceutically acceptable salt thereof, for the preparation of a medicament for the treatment of a cancer that expresses breast cancer resistant protein (BCRP) in a human subject in need of such a treatment.

2 Claims, No Drawings

USE OF IMATINIB (GLIVEC,STI-571) TO INHIBIT BREAST CANCER RESISTANCE PROTEIN (BCRP)-MEDIATED RESISTANCE TO THERAPEUTIC AGENTS

This application claims benefit of U.S. Provisional Application No. 60/417,915, filed Oct. 11, 2002.

The U.S. Government has a paid-up license in this invention and the right in limited circumstances to require the owner to license others on reasonable terms as provided for by the terms of Grant No. CA23099 awarded by the National Institute of Health.

SUMMARY

This invention relates to a method of utilizing imatinib to inhibit BCRP and BCRP-mediated resistance to therapeutic agents in the treatment of cancer. The invention further relates to a method of treating cancers that demonstrate BCRP-mediated resistance to one or more therapeutic agents wherein imatinib is co-administered with the therapeutic agent.

BACKGROUND

Imatinib is the generic name [International Non-proprietary Name] for the compound 4-(4-methylpiperazin-1-ylmethyl)-N-[4-methyl-3-(4-pyridin-3-yl)pyrimidin-2-ylamino)phenyl]-benzamide of the following formula I

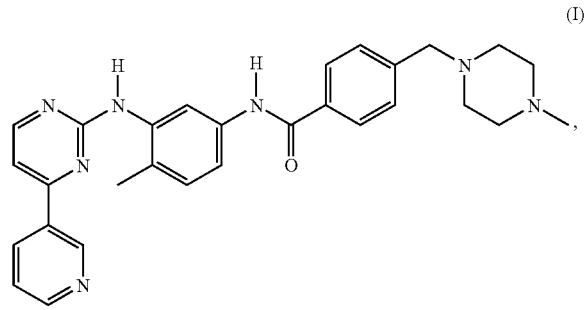

which has been approved, as its mesylate salt, for the treatment of chronic myeloid leukemia and gastrointestinal stromal tumors. Imatinib, its manufacture, its pharmaceutically acceptable salts, e.g. acid addition salts, and its protein kinase inhibiting properties are described in U.S. Pat. No. 5,521,184, which is hereby incorporated by reference. In the context of the present patent application, the term "imatinib" is meant to designated 4-(4-methylpiperazin-1-ylmethyl)-N-[4-methyl-3-(4-pyridin-3-yl)pyrimidin-2-ylamino)phenyl]-benzamide in its free form.

It has to be explained that otherwise the wording "imatinib" designates 4-(4-methylpiperazin-1-ylmethyl)-N-[4-methyl-3-(4-pyridin-3-yl)pyrimidin-2-ylamino)phenyl]-benzamide free base in the US only and that "imatinib" for the rest of the world corresponds to 4-(4-methylpiperazin-1-ylmethyl)-N-[4-methyl-3-(4-pyridin-3-yl)pyrimidin-2-ylamino)phenyl]-benzamide mesylate.

The preparation of imatinib and the use thereof, especially as an anti-tumor agent, are described in Example 21 of European patent application EP-A-0 564 409, which is hereby incorporated by reference.

The monomethanesulfonic acid addition salt of 4-(4-methylpiperazin-1-ylmethyl)-N-[4-methyl-3-(4-pyridin-3-yl) pyrimidin-2-ylamino)phenyl]-benzamide (hereinafter "imatinib mesylate") and a preferred crystal form thereof, e.g. the βcrystal form, are described in PCT patent application WO99/03854, hereby incorporated by reference. Possible pharmaceutical preparations, containing an effective amount of imatinib, e.g. imatinib mesylate, are also described in WO99/03854 and are well known in the prior art.

The present invention is derived from the discovery that imatinib also inhibits breast cancer resistance protein. Breast cancer resistance protein (BCRP) is a member of the ATP-binding cassette (ABC) transporter protein family. Such transporter proteins cause several anticancer drugs to efflux from cancer cells reducing the concentrations of the anticancer agent in these cells and thus reducing or eliminating the desirable anticancer effects of the agent in these resistant cancer cells. BCRP over-expression has been associated with resistance to anticancer agents such as doxorubicin, mitoxanthrone and especially camptothecin analogues and derivatives. In addition, the oral absorption of several therapeutic agents is inhibited by the BCRP ATP pump and inhibition of BCRP with imatinib provides a mechanism to improve the oral absorption of such therapeutic agents.

DETAILED DESCRIPTION

In a first aspect, the present invention relates to the use of imatinib, or a pharmaceutically acceptable salt thereof, for the manufacture of a medicament, to inhibit breast cancer resistance protein.

One aspect of the present invention is a method of inhibiting breast cancer resistance protein in a cell, which comprises placing the cell in contact with an effective amount of imatinib, or a pharmaceutically acceptable salt thereof. In accordance with this aspect, the cell is preferably a cancer cell that expresses BCRP.

The present invention further relates to a method of treating cancer that expresses BCRP in a human subject, which comprises administering a therapeutically effective amount of the anticancer agent and an effective BCRP-inhibiting amount of imatinib, or a pharmaceutically acceptable salt thereof, to the subject.

The present invention also relates to the use of imatinib or a pharmaceutically acceptable salt thereof for the manufacture of a medicament for the treatment of a cancer expressing the breast cancer resistant protein (BCRP).

The present invention further relates to the use of imatinib or a pharmaceutically acceptable salt thereof for the manufacture of a medicament for the treatment of a cancer over-expressing the breast cancer resistant protein (BCRP).

The present invention also relates to the use of imatinib or a pharmaceutically acceptable salt thereof for the manufacture of a medicament for preventing or reversing resistance to an anticancer agent in a human subject having a cancer that expresses BCRP.

The cancer to be treated according to the present invention can be, but is not limited to a cancer expressing the BCRP protein, a cancer over-expressing the BCRP protein, a cancer resistant to an anti-cancer agent which anti-cancer agent resistance is mediated by the expression of the BCRP protein, a cancer resistant to an anti-cancer agent which anti-cancer agent resistance is mediated by the over-expression of the BCRP protein, said cancer expressing or over-expressing BCRP can be a colon cancer, a breast cancer, a liver cancer, acute myeloid leukemia (AML), a gastric cancer, an ovarian cancer, a lung cancer, e.g. non-small cell lung cancer, a myeloma, e.g. human multiple myeloma, a fibrosarcoma.

The term "resistant to an anticancer agent" as used herein defines a reduction or loss of therapeutic effectiveness of an anticancer agent in the treatment of a cancer condition. The resistance of a cancer to an anticancer agent can be due to BCRP, e.g. to expression or over-expression of BCRP. Even low expression of BCRP can be responsible for the cancer resistance to an anticancer agent.

By "over-expressing" is meant that the level of expression of the breast cancer resistance protein or of its mRNA is higher, e.g. 1.5, 2, 4, 6, 10, 20 or more times higher, than the corresponding level of the BCRP protein in healthy patient or in corresponding normal tissues not harboring cancer or in cancer not resistant to anticancer agent.

The present invention relates to the use of imatinib or a pharmaceutically acceptable salt thereof for the manufacture of a medicament to improve the absorption of an orally-administered anticancer agent.

The present invention relates to the use of imatinib of formula I or a pharmaceutically acceptable salt thereof for the manufacture of a medicament for improving the absorption of an orally-administered anticancer agent by inhibiting BCRP in a patient having a cancer.

Because BCRP is involved in resistance to certain anticancer agents, another aspect of the present invention relates to a method of preventing or reversing resistance to an anticancer agent in a human subject having a cancer that expresses BCRP, which comprises administering a therapeutically effective amount of the anticancer agent and an effective BCRP-inhibiting amount of imatinib, or a pharmaceutically acceptable salt thereof, to the subject.

According to the present invention, a therapeutically effective amount of the anticancer agent, e.g. anthracycline cytotoxic agents, campothecin-derived topoisomerase I inhibitors, is administered in conjunction with imatinib. Therapeutically effective amounts of anticancer agents are known, or can be determined without undue experimentation, by one of skill in the art.

An effective BCRP inhibiting concentration of imatinib is generally achieved in a human subject by administering 100 mg to 1000 mg, e.g. 200 mg to 800 mg, e.g. 400 mg to 600 mg, of imatinib base daily to the subject. Imatinib is generally administered as a pharmaceutically acceptable salt, particularly as imatinib mesylate.

Whether the cancer expresses BCRP is determined by methods known in the art, such as those described in Kawabata el al., *Biochemical and Biophysical Research Communications,* 280, 1216-1223 (2001) and Erlichman et al., *Cancer Research,* 61, 379-748 (2001), both publications incorporated hereby by reference.

Generally, anticancer agents that are affected by BCRP-mediated resistance include the anthracycline cytotoxic agents and campothecin-derived topoisomerase I inhibitors. The anthracycline cytotoxic agents that are known to be affected by BCRP-mediated resistance include mitoxanthrone and doxorubicin. The camptothecin-derived topoisomerase I inhibitors include analogues and derivatives of camptothecin and homocampthecin, such as, topotecan, irinotecan also referred as CTP-11, and its metabolite 7-ethyl-10-hydroxycamptothecin also referred as SN-38, 9-aminocampththecin, 9-nitrocamptothecin, lurtotecan, diflomotecan, BAY38-3441, silatecans, such as 7-(2-trimethylsilyl) ethylcamptothecin also referred as BNP1350 and 10-hydroxy-7-t-butyldimethylsilylcamptothecin also referred as DB67, and various polymer-conjugated camptothecin derivatives, such as CT2016, DE310, T-0128 and PROTHECAN. Topotecan, irinotecan, mitoxanthrone and doxorubicin are particularly useful as the anticancer agent used according to the present invention.

The anthracycline cytotoxic agents and the campothecin-derived topoisomerase I inhibitors can be administered, e.g. in the form as they are marketed. Irinotecan can be administered, e.g. in the form as it is marketed, e.g. under the trademark CAMPTOSTAR™. Topotecan can be administered, e.g. in the form as it is marketed, e.g. under the trademark HYCAMTIN™.

In one embodiment, the present invention pertains to the use of imatinib or a pharmaceutically acceptable salt thereof for the manufacture of a medicament to improve the absorption of an orally-administered anticancer agent selected from the group comprising the anthracycline cytotoxic agents and the campothecin-derived topoisomerase I inhibitors.

In another embodiment, the present invention pertains to the use of imatinib or a pharmaceutically acceptable salt thereof for the manufacture of a medicament to improve the absorption of an orally-administered anticancer agent selected from the group comprising mitoxanthrone, doxorubicin, topotecan, irinotecan also referred as CTP-11, 7-ethyl-10-hydroxycamptothecin also referred as SN-38, 9-aminocampththecin, 9-nitrocamptothecin, lurtotecan, diflomotecan, BAY38-3441, silatecans, such as 7-(2-trimethylsilyl)ethylcamptothecin also referred as BNP1350 and 10-hydroxy-7-t-butyldimethylsilylcamptothecin also referred as DB67, CT2016, DE310, T-0128 and PROTHECAN.

The present invention pertains to the use of imatinib or a pharmaceutically acceptable salt thereof for the manufacture of a medicament to improve the absorption of an orally-administered anticancer agent selected from the group comprising mitoxanthrone, doxorubicin, topotecan, irinotecan and SN-38.

In another embodiment, the present invention pertains to the use of imatinib or a pharmaceutically acceptable salt thereof for the manufacture of a medicament to prevent or reverse resistance to an orally-administered anticancer agent selected from the group comprising the anthracycline cytotoxic agents and the campothecin-derived topoisomerase I inhibitors, in a cancer that expresses BCRP in a human subject having said cancer.

In another embodiment, the present invention pertains to the use of imatinib or a pharmaceutically acceptable salt thereof for the manufacture of a medicament to prevent or reverse resistance to an orally-administered anticancer agent selected from the group comprising mitoxanthrone, doxorubicin, topotecan, irinotecan also referred as CTP-11, 7-ethyl-10-hydroxycamptothecin also referred as SN-38, 9-aminocampththecin, 9-nitrocamptothecin, lurtotecan, diflomotecan, BAY38-3441, silatecans, such as 7-(2-trimethylsilyl)ethylcamptothecin also referred as BNP1350 and 10-hydroxy-7-t-butyldimethylsilylcamptothecin also referred as DB67, CT2016, DE310, T-0128 and PROTHECAN.

The present invention pertains to the use of imatinib or a pharmaceutically acceptable salt thereof for the manufacture of a medicament to prevent or reverse resistance to an orally-administered anticancer agent selected from the group comprising mitoxanthrone, doxorubicin, topotecan, irinotecan and SN-38.

Because BCRP is expressed in normal human intestinal villi, the BCRP ATP pump also has an adverse effect on the oral bioavailability of the anticancer agents and its inhibition improves the oral bioavailability of the agent.

Another aspect of this invention relates to a method of improving the absorption of an orally-administered anticancer agent, which comprises administering the anticancer agent and an effective BCRP-inhibiting amount of imatinib, or a pharmaceutically acceptable salt thereof, to the subject.

Example 1

Imatinib Mesylate is a Potent Inhibitor of BCRP and Reverses Topotecan Rresistance in Vitro Imatinib is assayed for its ability to selectively reverse BCRP-mediated resistance. Saos2 human osteosarcoma cells with no detectable expression of BCRP or P-glycoprotein are engineered to express similar levels of BCRP (Saos2BCRP#4), or non-functional mutant with a mutation in the Walker ATP binding motif (Saos2BCRPMut#10). Saos2 cells transfected with pcDNA3 vector are used as an additional control. The $IC_{50}$ concentrations of topotecan are 9 nM, 16 nM and 167 nM for Saos2Mut#10, Saos2pcDNA and Saos2BCRP#4 respectively. Imatinib selectively sensitized Saos2BCRP#4 cells, almost completely reversing topotecan resistance at a concentration of 1 µM. To define the concentration of imatinib required to reverse topotecan resistance by 50%, Saos2BCRP#4 cells are exposed to topotecan for 5 days in the presence of increasing concentrations of imatinib (10-1000 nM). 50% reversal of BCRP resistance is obtained at around 170 nM. Imatinib is an potent inhibitor of BCRP-mediated resistance to topotecan. As BCRP may inhibit the absorption of orally administered topotecan and irinotecan.

Table 1 discloses the effect of imatinib on the $IC_{50}$ for topotecan in three human cancer cell lines. The data demonstrates a synergistic effect between topotecan and imatinib and complete reversal of BCRP-mediated resistance to topotecan in the BCRP expressing SaosBCRP#4 cell line.

TABLE 1

The effect of imatinib on the $IC_{50}$ for topotecan in three human cancer cell lines: a vector control Saos2pcDNA#3#2, a cell line expressing functional BCRP Saos2BCRP#4, and a cell line equivalently expressing a non-functional mutant BCRP, Saos2BCRPMUT#10. Results show the concentration of topotecan causing 50% growth inhibition in the absence (0) or presence of imatinib at the concentrations shown.

|  | Saos2 pcDNA#3#2 | Saos2 BCRP#4 | Saos2 BCRPMUT#10 |
|---|---|---|---|
| topotecan alone | 20 nM | 254 nM | 9 nM |
| 1 µM imatinib + topotecan | 23 nM | 35 nM | 18 nM |
| 3 µM imatinib + topotecan | 20 nM | 24 nM | 9.9 nM |
| 5 µM Imatinib + topotecan | 23 nM | 22 nM | 15 nM |
| imatinib alone | 7.3 mM | 9.6 mM | 9.5 nM |

Example 2

Reversal of BCRP-Mediated Resistance to SN-38 by imatinib

TABLE 2

Reversal of BCRP-mediated resistance to SN-38 by imatinib. BCRP#4 are Saos2 cells expressing functional BCRP, pcDNA are Saos2 cells with a control vector, MUT#10 are Saos2 cells expressing non-functional BCRP. Results show the concentration of SN-38 causing 50% growth inhibition in the absence (0) or presence of imatinib at the concentrations shown.

| | $IC_{50}$ nM | | |
|---|---|---|---|
| Imatinib in µM | Saos2BCRP#4 | Saos2pcDNA#3#2 | Saos2MUT#10 |
| 0 | >100 | 2.9 | 1.7 |
| 0.1 | 82 | 2.7 | 1.7 |
| 0.3 | 29 | 2.7 | 1.6 |
| 1.0 | 14 | 3.3 | 1.7 |
| 3.0 | 7 | 3.7 | 1.6 |

Example 3

Effect of Imatinib on Irinotecan Pharmacokinetics in Mice

The experiment is performed on non-tumored mice after a single oral administration of imatinib of 50 mg/kg and a single oral administration of irinotecan (IRN) of 10 mg/kg.

TABLE 3

Effect of imatinib on irinotecan Pharmacokinetics in Mice. Mice are dosed orally with CPT-11 alone or immediately after a single oral dose of Imatinib (50 mg/kg). Plasma levels of irinotecan (IRN) and SN-38, the active metabolite, are determined.

| | Without imatinib | With imatinib |
|---|---|---|
| IRN Cl (L/h/m2) | 16.7 ± 3.3 | 11.2 ± 4.0 |
| Ka (hr-1) | 1.65 ± 0.3 | 1.6 ± 0.2 |
| F | 0.09 ± 0.02 | 0.23 ± 0.02 |
| SN-38 (ng/hr/ml) | 263 | 775 |

Those results suggest that administration of imatinib enhances oral bioavailability of irinotecan and increases exposure to SN-38 by 3 fold. Ci: rate of clearance; Ka: absorption rate; F: calculated bioavailability (relative to intravenous dosing).

Example 4

Capsules with 4-[(4-methyl-1-piperazin-1-ylmethyl)-N-[4-methyl-3-[[4-(3-pyridinyl)-2-pyrimidinyl]amino]phenyl]benzamide mesylate, β-crystal Form Capsules containing 119.5 mg of imatinib mesylate corresponding to 100 mg of imatinib free base as active substance are prepared in the following composition:

| Composition | |
|---|---|
| Imatinib mesylate | 119.5 mg |
| Cellulose MX GR | 92 mg |
| Crospovidone XL | 15 mg |
| Aerosil 200 | 2 mg |
| Magnesium stearate | 1.5 mg |
| | 230 mg |

The capsules are prepared by mixing the components and filling the mixture into hard gelatin capsules, size 1.

The invention claimed is:

1. A method of treating a patient with an osteosarcoma that has a BCRP-mediated resistance to a camptothecin-derived topoisomerase I inhibitor, which comprises administering the camptothecin-derived topoisomerase I inhibitor to the patient and reversing the BCRP-mediated resistance to the camptothecin-derived topoisomerase I inhibitor by co-administering to the patient an effective BCRP-inhibiting amount of imatinib or a pharmaceutically acceptable salt thereof.

2. A method of claim 1 wherein the camptothecin-derived topoisomerase I inhibitor is selected from the group consisting of topotecan and irinotecan.

* * * * *